US011877798B2

(12) United States Patent
Ito (10) Patent No.: US 11,877,798 B2
(45) Date of Patent: Jan. 23, 2024

(54) OPHTHALMOLOGIC IMAGING APPARATUS (71) Applicant: NIDEK CO., LTD., Aichi (JP)

(72) Inventor: Koichi Ito, Aichi (JP)

(73) Assignee: NIDEK CO., LTD., Aichi (JP)

( * ) Notice: Subject to any disclaimer, the term of this patent is extended or adjusted under 35 U.S.C. 154(b) by 607 days.

(21) Appl. No.: 17/035,910

(22) Filed: Sep. 29, 2020

(65) Prior Publication Data

US 2021/0093187 A1  Apr. 1, 2021

(30) Foreign Application Priority Data

Sep. 30, 2019  (JP) ................ 2019-180052

(51) Int. Cl.
*A61B 3/10* (2006.01)
*A61B 3/00* (2006.01)

(52) U.S. Cl.
CPC ............ *A61B 3/102* (2013.01); *A61B 3/0008* (2013.01); *A61B 3/0025* (2013.01); *A61B 3/0058* (2013.01)

(58) Field of Classification Search
CPC ....... A61B 3/102; A61B 3/008; A61B 3/0025; A61B 3/0058
USPC .......................................... 351/221
See application file for complete search history.

(56) References Cited

U.S. PATENT DOCUMENTS

| 2002/0026179 | A1* | 2/2002 | Toh ................. | A61F 9/00804 606/5 |
| 2009/0149742 | A1* | 6/2009 | Kato ................ | A61B 5/0066 600/425 |
| 2010/0220287 | A1* | 9/2010 | Sumiya ............ | A61B 3/10 351/221 |
| 2011/0267340 | A1* | 11/2011 | Kraus ............... | A61B 3/0025 345/419 |
| 2014/0107960 | A1  | 4/2014 | Oritz Egea et al. | |
| 2014/0347627 | A1* | 11/2014 | Imamura .......... | A61B 3/14 351/246 |
| 2017/0188816 | A1* | 7/2017 | Ono ................. | G16H 30/20 |

(Continued)

FOREIGN PATENT DOCUMENTS

| JP | 2014-57899 A | 4/2014 |
| JP | 2014-512242 A | 5/2014 |

(Continued)

OTHER PUBLICATIONS

Office Action dated Apr. 25, 2023 by the Japanese Patent Office in counterpart Japanese Patent Application No. 2019-180052.

*Primary Examiner* — William R Alexander
*Assistant Examiner* — Sharrief I Broome
(74) *Attorney, Agent, or Firm* — Sughrue Mion, PLLC (57) ABSTRACT

An ophthalmologic imaging apparatus having an OCT optical system for acquiring OCT data of a tissue of a subject eye based on a spectral interference signal of measurement light emitted to the tissue and reference light. The apparatus further has a second optical system for acquiring a front image of the tissue; an optical element having asymmetry and arranged on a common optical path of the OCT optical system and the second optical system; and an arithmetic controller that associates an OCT data acquisition position with coordinates of the front image while taking at least a difference in distortion caused by the optical element between the OCT optical system and the second optical system into consideration.

8 Claims, 8 Drawing Sheets

(56) References Cited

U.S. PATENT DOCUMENTS

2019/0038127 A1 2/2019 Ito
2021/0027467 A1* 1/2021 Hirokawa ............. G06T 7/0012

FOREIGN PATENT DOCUMENTS

| JP | 2014-140489 A | 8/2014 |
| JP | 2017-29282 A | 2/2017 |
| JP | 2017-205658 A | 11/2017 |
| JP | 2019-25255 A | 2/2019 |

* cited by examiner

| ANGLE OF VIEW ($\Theta x, \Theta y$) | SWING ANGLE (X, Y) |
|---|---|
| (0,0) | (a,b) |
| (0,1) | (c,d) |
| (0,2) | (e,f) |
| ⋮ | ⋮ |
| (110,110) | (p,q) |

OPHTHALMOLOGIC IMAGING APPARATUS

CROSS-REFERENCE TO RELATED APPLICATION

The present application claims priority from Japanese Patent Application No. 2019-180052 filed on Sep. 30, 2019, the entire content of which is incorporated herein by reference.

TECHNICAL FIELD

The present disclosure relates to an ophthalmologic imaging apparatus.

BACKGROUND

In the field of ophthalmology, an optical coherence tomography (OCT), which is an apparatus for imaging OCT data of tissues of a subject eye, is widely used. As a type of such apparatus, an apparatus that includes an optical system (for example, an observation optical system) for capturing a front image of the fundus is known in addition to an OCT optical system. For example, the front image of the fundus is used for planning an OCT data acquisition position before imaging or for checking the OCT data after imaging (refer to JP-A-2014-57899).

In OCT imaging in the field of ophthalmology, a structure and thickness of the tissue in a center part of the fundus, such as a region of macular-optic disc, for example, are the main points of interest in diagnosis and observation. However, in recent year, the interest is increasing not only in the center part of the fundus but also in a peripheral part of the fundus. Therefore, for example, an optical system for widening the imaging range of the OCT data has been proposed by the present inventors (refer to JP-A-2019-25255).

In some cases, an optical element having asymmetry may be arranged on a common optical path of the OCT optical system and the optical system that captures a front image of the fundus. In this case, the inventors have found that a difference in distortion may occur between the two optical systems due to the optical element. The influence of the difference in distortion is more likely to be emphasized in the peripheral part than in the center part of the imaging range. As a result, the coordinates of the front image and the OCT data acquisition position may not be accurately associated with each other over the entire imaging range. The problem of this association accuracy over the entire imaging range becomes clearer as the angle of view becomes wider, however, this problem has been overlooked in a situation where the OCT imaging is mainly used for imaging the center part of the fundus in the related art.

SUMMARY

The present disclosure has been made in view of the problems in the related art, and an object of the present disclosure is to provide an ophthalmologic imaging apparatus in which the association accuracy between the coordinates of the front image and the OCT data acquisition position is improved.

An ophthalmologic imaging apparatus according to an aspect of the present disclosure includes: an OCT optical system for acquiring OCT data of a tissue of a subject eye based on a spectral interference signal of measurement light emitted to the tissue and reference light; a second optical system for acquiring a front image of the tissue; an optical element having asymmetry and being arranged on a common optical path of the OCT optical system and the second optical system; and arithmetic controller configured to associate an OCT data acquisition position with coordinates of the front image while taking at least a difference in distortion caused by the optical element between the OCT optical system and the second optical system into consideration.

DETAILED DESCRIPTION

<Outline>

An illustrative embodiment of the present disclosure will be described. Items classified by < > below can be used independently or in association with each other.

First, an ophthalmologic imaging apparatus according to the illustrative embodiment will be described. The ophthalmologic imaging apparatus includes an OCT optical system, a second optical system, and an arithmetic control means (an arithmetic control unit).

<OCT Optical System>

In the present illustrative embodiment, the OCT optical system is used to acquire OCT data of tissues of a subject eye. The OCT optical system detects a spectral interference signal between the measurement light emitted to the tissues of the subject eye and the reference light. The OCT data is generated and acquired by processing the spectral interference signal.

In addition, the OCT optical system may include at least one of a light splitting unit, a scanning unit (also referred to as an optical scanner), and a detector. The light splitting unit splits the light from the OCT light source into the measurement light and the reference light. The scanning unit is a device for scanning the tissues of the subject eye with the measurement light. The scanning unit may be capable of performing the scanning with the measurement light in two directions that intersect each other. For example, two galvanometer mirrors that perform the scanning with the measurement light in each of the two directions may be provided as a scanning unit. The detector outputs the spectral interference signal by receiving the measurement light guided by the subject eye and the reference light. The OCT optical system may perform the scanning with the measurement light along multiple scan lines that are predetermined on the tissues of the subject eye to image the OCT data for each of the multiple scan lines. The scan line may be set at any position based on an instruction from the examiner. In addition, the scan line corresponding to the scan pattern may be set by selecting one of a plurality of predetermined scan patterns. Various scan patterns such as line, cross, multi, and map are known.

<Second Optical System>

The second optical system is used for acquiring the front image of the tissues of the subject eye. The second optical system may emit second light from a second light source to the tissues of the subject eye and may acquire the front image based on the reflection light of the second light. The front image may be used, for example, for at least one of planning, setting, and confirming the OCT data acquisition position. At this time, the OCT data acquisition position may be displayed on the front image by the control unit in a superimposed manner.

The second optical system includes at least the second light source and the detector. The second optical system may be a scanning type optical system or a non-scanning type optical system. The wavelength bands of the second light and the light from the OCT light source may be different from each other. As a result, an optical path of the OCT optical system (first optical path) and an optical path of the second optical system (second optical path) may be combined into one optical path by a dichroic mirror. As a result, the dichroic mirror causes an optical axis of the OCT optical system and an optical axis of the second optical system to substantially coincide with each other and guides the light to the subject eye. In this case, an objective optical system, which is shared between the optical path of the OCT optical system and the second optical system, may be arranged between the dichroic mirror and the subject eye. In addition, the OCT light source and the detector in the OCT optical system and the second light source and the detector in the second optical system may be arranged in an independent optical path respectively.

<Association Between OCT Data Acquisition Position and Coordinates of Front Image>

Incidentally, the dichroic mirror is one of the optical element having asymmetry because it is arranged in tilted with respect to the optical axis. The difference in distortion between the OCT optical system and the second optical system is generated due to the dichroic mirrors.

For example, the dichroic mirrors may cause asymmetrical optical axis distortion for at least one of the OCT optical system and the second optical system. In this case, any one of a relationship between a swing angle of the scanning unit and the angle of view in the OCT optical system and a relationship between the coordinates on the front image and the angle of view becomes a non-linear relationship. As a result, the relationship between the swing angle of the scanning unit in the OCT optical system and the coordinates on the front image becomes non-linear. In this case, if the coordinates on the front image and the OCT data acquisition position are linearly associated in the center part of the imaging range, a large error occurs between the actual OCT data acquisition position and the acquisition position indicated on the front image in the peripheral part.

In recent years, the OCT capable of imaging in a wide angle of view has been proposed, but this kind of apparatus is more likely to have a problem of above-described influence of the difference in distortion. The wide angle of view here means that the peripheral part of the fundus positioned on the peripheral side between the macula and the optic disk is included in the imaging range in the OCT optical system. Here, in a standard fundus of an adult, a distance on the retina between the macula and the optic disk is said to be approximately 14 mm, which is converted to approximately 47° as a horizontal imaging angle of view. That is, when the horizontal imaging angle of view in the OCT optical system is wider than 47°, the influence of the difference in distortion easily becomes a problem.

In addition, for example, a difference in distortion may occur due to an optical axis deviation between the OCT optical system and the second optical system due to the dichroic mirror.

On the other hand, the arithmetic control unit in the present example associates the OCT data acquisition position with the coordinates of the front image while taking the difference in distortion between the OCT optical system and the second optical system caused by the asymmetric optical element such as a dichroic mirror into consideration. In this way, the coordinates on the front image and the OCT data acquisition position can be favorably associated with each other at each position.

In this case, the arithmetic control unit may associate the OCT data acquisition position with the coordinates of the front image based on predetermined association information. At this time, the OCT data acquisition position may be associated with the coordinates of the front image in a non-linear manner based on the association information.

The association information represents, for example, an association relationship between the swing angle and the coordinates on the front image, which is set in advance for each swing angle in the optical scanner. The association information may indicate a non-linear association relationship between the swing angle and the coordinates on the front image.

More specifically, the association information may be a combination of following first association information and second association information. For example, the first association information is information representing an association relationship between the swing angle and the angle of view, which is set in advance for each swing angle in the optical scanner. In addition, the second association information is information representing an association relationship between the coordinates on the front image and the angle of view. By combining the first association information and the second association information, the swing angle in the optical scanner and the coordinates of the front image can be associated with each other through the angle of view.

A chromatic aberration of magnification between the OCT optical system and the second optical system also influences the difference in distortion. On the other hand, the influence of chromatic aberration of magnification may be collectively corrected by using the above-described association information. The chromatic aberration of magnification may occur mainly due to the objective optical system when the objective optical system is a refractive system.

In the present illustrative embodiment, the angle of view in each association information is based on the same position as a reference (origin). For example, the angle of view may have a value based on a point on an optical path common in the OCT optical system and the second optical system. For example, a position of an exit pupil may be the reference.

<Superimposed Display of OCT Data Acquisition Position on Front Image>

The arithmetic control unit may display a graphic indicating the OCT data acquisition position on the front image in a superimposed manner as a result of above-described association. The graphic mode can be appropriately selected from various modes according to the scanning method. For example, any one of a dot graphic indicating a scan point, a line graphic indicating a scan line, a two-dimensional graphic indicating a map scan range, or the like may be appropriately applied. The trajectory of the measurement light on the tissues of the subject eye is indicated by the linear graphic and the two-dimensional graphic.

In this case, the arithmetic control unit may generate a front image in which pixels are arranged at equal intervals with respect to the angle of view. The graphic indicating the OCT data acquisition position is displayed on the front image in a superimposed manner. In the front image where the pixels are arranged at equal intervals with respect to the angle of view, the difference in angle of view between the adjacent pixels is constant in each of the vertical direction and the horizontal direction. As a result, for example, the OCT data acquisition position can be accurately associated with each pixel on the front image.

In addition, the arithmetic control unit may display a scan line along the main scanning line (here, the horizontal scanning line), which is set at a position away from the optical axis, as a curved graphic in a superimposed manner on the front image. The scanning position of the measurement light in the tissue and the scanning position on the front image are associated with each other via a curve.

At this time, a curve indicating the scan line may be obtained based on the value of the swing angle of the scanning unit associated with the scan line and the association information. For example, a line passing through the swing angle associated with the start point and the end point of the scan line, the position of coordinates on the front image associated with the swing angle, and the position of coordinates on the front image associated with the intermediate value of the swing angle, may be obtained. The graphic indicating the line may be displayed on the front image of the fundus in a superimposed manner.

In addition, as a graphic indicating the scan line connecting the two points, the arithmetic control unit may generate a trajectory of measurement light when the scanning unit is driven at a constant angular velocity in scanning between the two points, based on the above-described association information. Here, when a device capable of operating at a constant angular velocity such as a galvanometer mirror is applied as the scanning unit, the trajectory of the measurement light can be accurately drawn on the front image.

The two points may be the start point and the end point of the scan line, or may be any two points on the scan line including the middle point.

<Driving Control of Scanning Unit>

In the description above, in combination with the OCT data acquisition position, the graphic indicating the acquisition position superimposed on the front image is processed. However, it is not necessarily limited thereto. For example, when planning the OCT data acquisition position, any scan line may be set on the front image. For example, the scan line may be indicated by a straight line on the front image. When the planning of the OCT data acquisition position is completed, the coordinate information on the front image corresponding to each position of the scan line may be acquired. The arithmetic control unit may perform the driving control of the scanning unit based on the coordinate information on the front image corresponding to each position of the scan line and the association information. In this way, the acquisition position of OCT on the front image is accurately traced on the fundus by the measurement light.

<Regarding Other Optical Element Having Asymmetry>

In the description above, the dichroic mirror is exemplified as the optical element having asymmetry, but the optical element is not necessarily limited thereto. For example, an optical element having asymmetry may be an eccentrically arranged objective optical system. In this case, the objective optical system includes an eccentric optical axis (including tilt) with respect to the optical axes of the OCT optical system and the second optical system.

Example

Next, an example will be described. A fundus imaging apparatus (OCT device) 1 illustrated in the drawing is a kind of ophthalmologic imaging apparatus in the illustrative embodiment.

<Overall Configuration of Fundus Imaging Apparatus>

Figure 1:
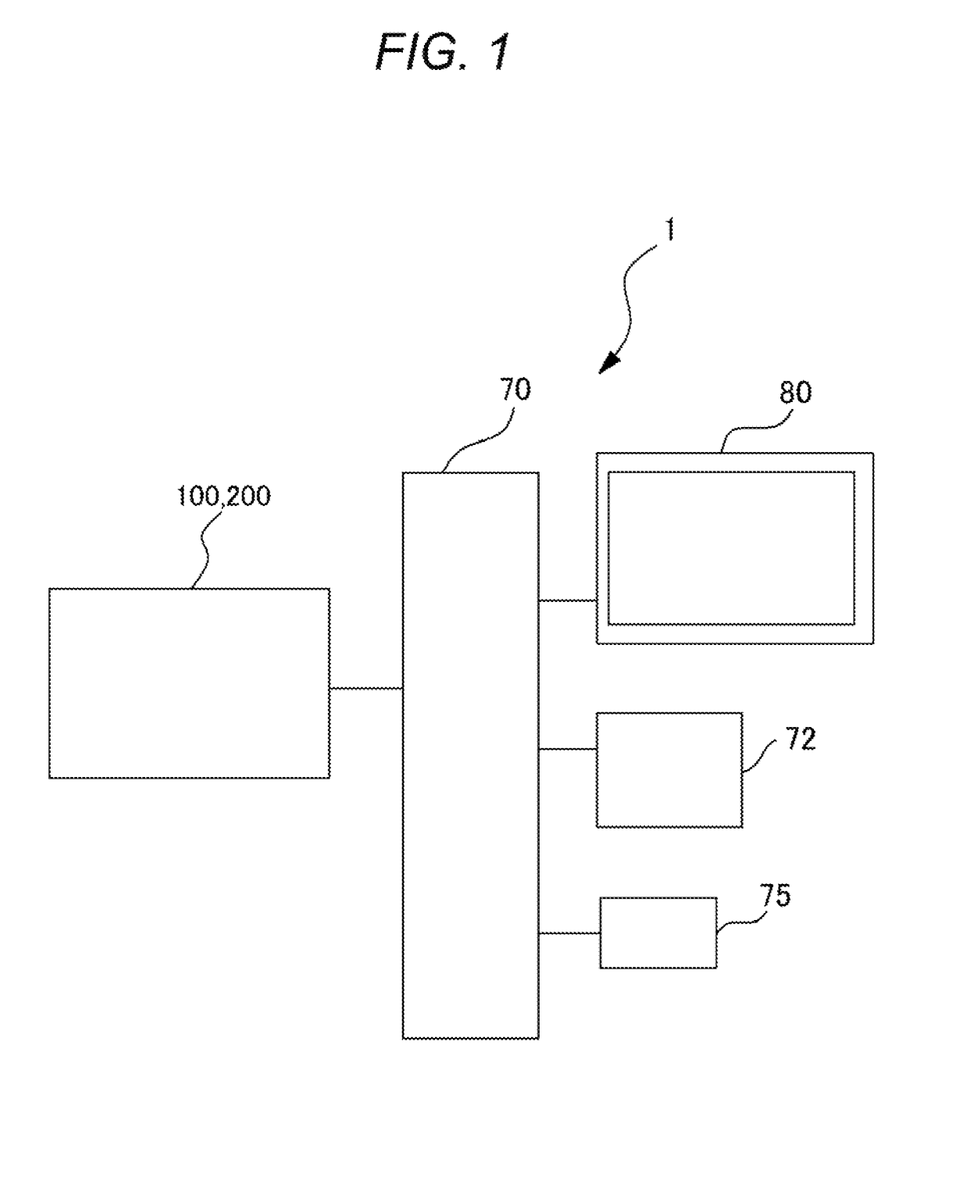
FIG. 1 is a diagram illustrating a schematic configuration of an ophthalmologic imaging apparatus according to an example.

First, with reference to FIG. 1, a schematic configuration of an ophthalmologic imaging apparatus 1 (hereinafter referred to as "the apparatus 1") will be described.

The apparatus 1 includes an OCT optical system (interference optical system) 100, a second optical system 200, and a control unit 70. In the present illustrative embodiment, the OCT optical system 100 is used for non-invasively obtaining a tomographic image of a predetermined part of the subject eye E by using an optical interference technology. In addition, the second optical system 200 is used for obtaining a front image of a predetermined part of the subject eye E. Hereinafter, in the present illustrative embodiment, the predetermined part of the subject eye E is a fundus part Ef of the subject eye E.

As an example, each of the OCT optical system (interference optical system) 100 and the second optical system 200 in the present example can image the fundus with an angle of view of 110°. This is only an example of an optical system capable of imaging with a wide angle of view, and the angle of view is not necessarily limited to this.

The control unit 70 is configured with a CPU and various memories. The control unit 70 may also serve as an image processing unit in the apparatus 1.

Additionally, the apparatus 1 may include a storage unit 72, an operation unit 75, and a monitor 80. Each unit may be electrically connected to the control unit 70.

In the present example, the association information may be stored in the storage unit 72 in advance.

The operation unit 75 may be a pointing device such as a mouse and a touch panel, or may be another user interface.

<Optical System>

Next, the optical system of the apparatus 1 will be described with reference to FIG. 2. In the description below, as illustrated in FIG. 2, the depth direction of the subject eye E is referred to as the Z direction (working distance direction), the horizontal direction is referred to as the X direction, and the vertical direction is referred to as the Y direction.

Figure 2:
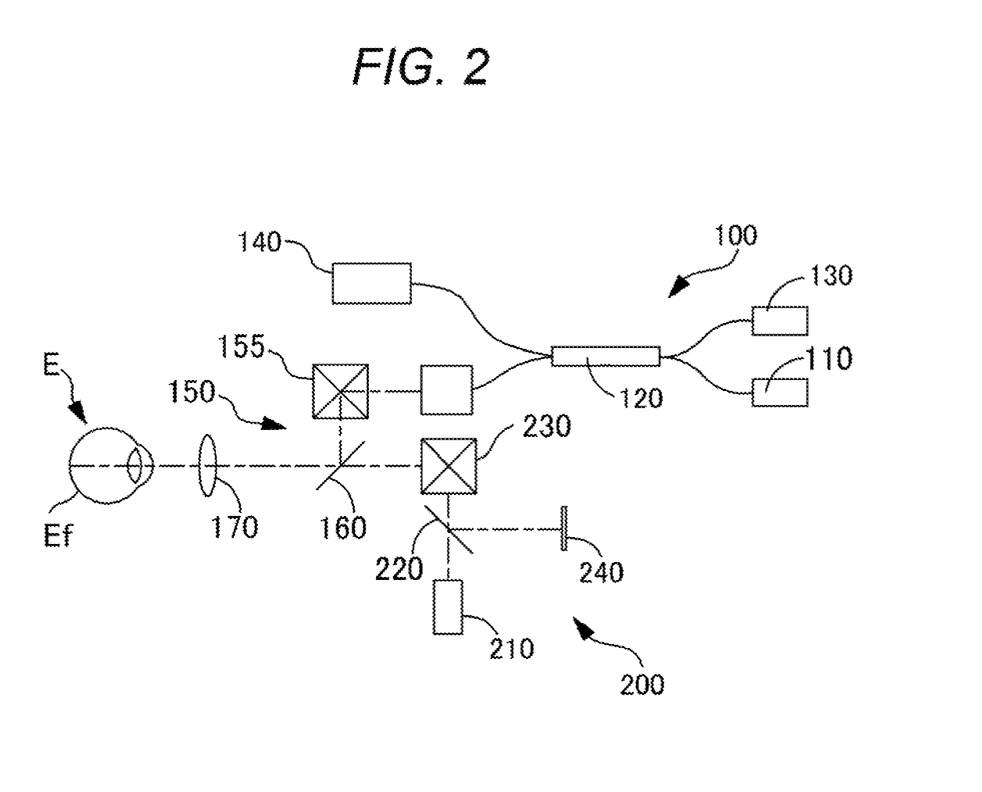
FIG. 2 is a diagram illustrating a main optical system of the ophthalmologic imaging apparatus.

As illustrated in FIG. 2, in the apparatus 1, the OCT optical system 100 and the second optical system 200 share the dichroic mirror 160 and the objective optical system 170. The optical paths of the OCT optical system 100 and the second optical system 200 are combined and branched by the dichroic mirror 160 in a wavelength selective manner. In the present example, the wavelength bands of the measurement light by the OCT optical system 100 and that of the second light by the second optical system 200 are different from each other. As illustrated in FIG. 2, the dichroic mirror 160 may transmit the measurement light from the OCT optical system 100 and reflect the second light from the second optical system 200.

<OCT Optical System>

Hereafter, as an example, the OCT optical system 100 to which the SD-OCT is applied is illustrated. However, it is not necessarily limited to this. The OCT optical system 100 may be, for example, an SS-OCT optical system, or may be an OCT optical system based on another imaging principle.

The OCT optical system 100 illustrated in FIG. 2 includes an OCT light source 110, a light splitter 120, a detector 130, a reference optical system 140, and a light guiding optical system 150. Although not illustrated and described in the present example, the OCT optical system 100 may include various adjustment units such as an optical path length adjustment unit, a polarization adjustment unit, and a focus adjustment unit.

In SD-OCT, the OCT light source 110 emits low coherent light. The light emitted from the OCT light source 110 is split into the measurement light and the reference light by the light splitter 120. In the present example, a coupler (splitter) is used as the light splitter 120. The measurement light is guided to the fundus of the subject eye via the light guiding optical system 150, and the reference light is guided to the reference optical system 140.

A reflection optical system is used as the reference optical system 140 illustrated in FIG. 2, but not necessarily limited thereto. For example, the reference optical system 140 may be formed by a transmission optical system. In the reference optical system 140, the reference light is folded back by a mirror (not illustrated), and is incident on the detector 130 after being combined with the return light of the measurement light by the light splitter 120.

In the SD-OCT, the detector 130 is a spectrometer (a spectral detector). The detector 130 outputs a spectral interference signal of the return light and the reference light. The OCT data of the fundus is acquired based on the spectral interference signal of the return light and the reference light.

In the present example, the optical system arranged between the light splitter 120 and the subject eye is referred to as a light guiding optical system 150. The scanning unit (optical scanner) 155, the dichroic mirror 160, and the objective optical system 170 are arranged in the light guiding optical system 150.

The scanning unit 155 is used to change the OCT data acquisition position on the fundus. The scanning unit 155 may be used to scan the fundus (inspection object) with the measurement light two-dimensionally (XY direction). In the present example, the scanning unit 155 includes two optical scanners of which scanning directions are different from each other. As an example, in the description below, an X galvanometer mirror for scanning in the X direction and a Y galvanometer mirror for scanning in the Y direction may be included.

The objective optical system 170 forms a turning point of the measurement light and guides the measurement light to the fundus of the subject eye via the turning point. With respect to the objective optical system 170, the scanning unit 155 is arranged at a position conjugate with the pupil of the subject eye. Accordingly, the measurement light is turned at a point on the pupil as a turning point according to the driving amount of the scanning unit 155.

In the present disclosure, it is assumed that "conjugate" is not necessarily limited to a perfect conjugate relationship, but may include "substantially conjugate". That is, within a range allowed in relation to the purpose of use of the fundus image (for example, observation, analysis, or the like), a case where the position is displaced from the complete conjugate position is also included in "conjugate" in the present disclosure.

<Second Optical System>

The second optical system 200 is used for acquiring the front image of the fundus of the subject eye. The second optical system 200 in the present example is a scanning type optical system (SLO optical system: scanning light ophthalmoscope optical system). Particularly, a case will be described, in which a two-dimensional scan type SLO optical system that two-dimensionally scans the fundus with a spot-shaped light flux is applied as the second optical system 200.

In the present example, the second optical system 200 also serves as an observation optical system that acquires an observation image as a front image. The observation image may be a moving image and may be displayed on the monitor 80 in real time. Also, the front image acquired based on a predetermined trigger (for example, a release signal) may be stored in the memory 72 as a captured image.

The second optical system 200 includes a second light source 210, a beam splitter 220, a scanning unit 230, a dichroic mirror 160, an objective optical system 170, and a detector (light receiving element) 240. The second light source 210 may emit infrared light and visible light as the second light. The infrared light may be emitted when acquiring the observation image. The second light passes through the beam splitter 220, the scanning unit 230, the dichroic mirror 160, and the objective optical system 170 in order, and is guided to the fundus of the subject eye.

The beam splitter 220 may be a perforated mirror or a half mirror.

The scanning unit 230 is a device for scanning the fundus in the XY direction with the second light. In the present example, the scanning unit 230 is used for performing raster-scanning on the fundus with the second light. In the present example, the scanning unit 230 includes a high-speed driving optical scanner for main scanning and an optical scanner for sub-scanning. As the optical scanner for main scanning, for example, a resonant scanner or a polygon mirror may be used. As the optical scanner for sub-scanning, for example, a galvanometer mirror or the like may be used.

With respect to the objective optical system 170, the scanning unit 230 is arranged at a position conjugate with the pupil of the subject eye. As a result, the turning point of the second light is formed on the pupil of the subject eye, and the second light is turned with the turning point as a center.

The fundus reflected light of the second light is guided to the beam splitter 220 by tracing back the route at the time of projection. In the present example, the light reflected by the beam splitter 220 is received by the detector 240. In the two-dimensional scan type SLO optical system, the detector 240 may be a point light receiving element. Furthermore, a confocal diaphragm (not illustrated) may be arranged at a fundus conjugate position between the detector 240 and the beam splitter 220.

The received light signal from the detector 240 is input to the control unit 70. The control unit 70 generates and acquires a front image of the fundus based on the received light signal from the detector 240.

<Regarding Association Information>

In the present example, the dichroic mirror 160 is arranged in a tilted manner with respect to the optical axis L of each optical system 100 and 200. When the second light passes through the dichroic mirror 160, the light beams are refracted on the surface of the dichroic mirror 160. In the second optical system 200, when two light fluxes symmetrical to the optical axis LI with respect to the Y scanning direction are incident on the dichroic mirror 160, the two light beams asymmetrically bend at the dichroic mirror 160. As a result, the association relationship between the swing angle of the Y galvanometer mirror in the scanning unit 230 and the coordinates of the front image becomes non-linear in the Y scanning direction. That is, an asymmetrical distortion is given to the aberration in the second optical system 200. On the other hand, before and after the measurement light is reflected on the surface of the dichroic mirror 160, the association relationship between the swing angle of the Y galvanometer mirror and the OCT data acquisition position in the scanning unit 150 is linear in the Y scanning direction. Accordingly, in the present example, the association relationship between the swing angle of the scanning unit 150 in the OCT optical system 100 and the coordinates of the front image is non-linear in the Y scanning direction.

On the contrary, in the present example, by using the association information, it is possible to appropriately associate the coordinates of the front image with the OCT data acquisition position.

In the present example, the association information for OCT (the first association information in the present example) and the association information for SLO (the second association information in the present example) are stored in storage unit 72 as the association information.

Figure 3:
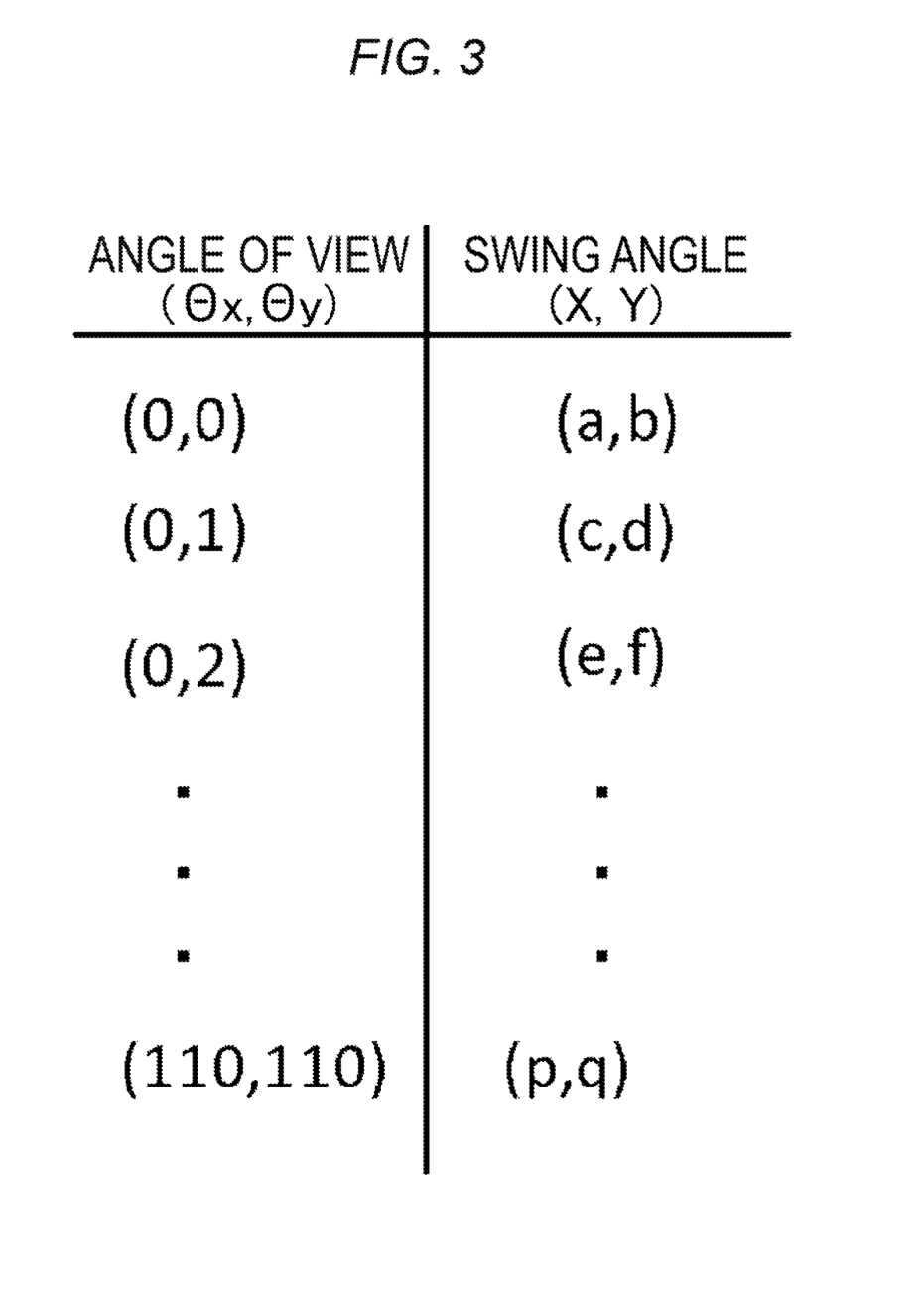
FIG. 3 is a diagram for explaining association information.

The association information for OCT indicates the association relationship between the swing angle (x, y) of the scanning unit 150 and the angle of view ($\theta x$, $\theta y$) in the OCT optical system 100 for each angle of view (refer to FIG. 3). Similarly, the association information for SLO indicates the association relationship between the swing angle (x, y) of the scanning unit 230 and the angle of view ($\theta x$, $\theta y$) in the second optical system 200 for each angle of view. The swing angle (x, y) of the scanning unit 230 in the association information for SLO has a one-to-one correspondence with the coordinates on the front image. That is, the association information for SLO in the present example indicates the association relationship between the angle of view ($\theta x$, $\theta y$) and the coordinates on the front image.

Each of such association information for OCT and association information for SLO may be a lookup table in which the association relationship between the swing angle and the angle of view is defined for each angle of view. In addition, each of the association information may be a function in which the association relationship between the swing angle and the angle of view is defined.

The association information in the present example may be information based on simulation by a light beam tracing method, for example. In addition, for example, the association information may be information based on calibration using a schematic eye for calibration of the angle of view. In this case, the association information may be unique information for each apparatus.

The influence of asymmetrical distortion (that is, the non-linearity of the association relationship between the swing angle of the scanning unit 230 in the Y direction and the coordinates of the front image) in the second optical system 200 can be corrected based on the association information for SLO. For example, the front image from which the scanning lines are acquired for each constant swing angle may be coordinate-converted based on the association information for SLO so as to be expressed in a coordinate system that is symmetric with respect to the angle of view ($\theta x$, $\theta y$). At this time, non-linear coordinate conversion is performed at least in the Y direction. Not limited to the image processing, the association information for SLO may be considered in the control parameter of the scanning unit 230 in the Y direction. In this case, the control parameters of the scanning unit 230 in the Y direction are reverse-calculated based on the association information for SLO so that the front image of the fundus expressed in a coordinate system symmetrical with respect to the angle of view ($\theta x$, $\theta y$) is acquired.

The difference in chromatic aberration of magnification between the OCT optical system 100 and the second optical system 200 also affects the error in the association relationship between the coordinates of the front image and the OCT data acquisition position. On the other hand, by using the association information described above, the influence of the chromatic aberration of magnification can also be corrected collectively. In the second optical system 200, when the second light source 210 emits the light of multiple wavelengths, since the influence of the chromatic aberration of magnification is different for each wavelength component (each channel), the association information for SLO may be prepared for each wavelength component.

<Explanation of Operation>

Figure 4:
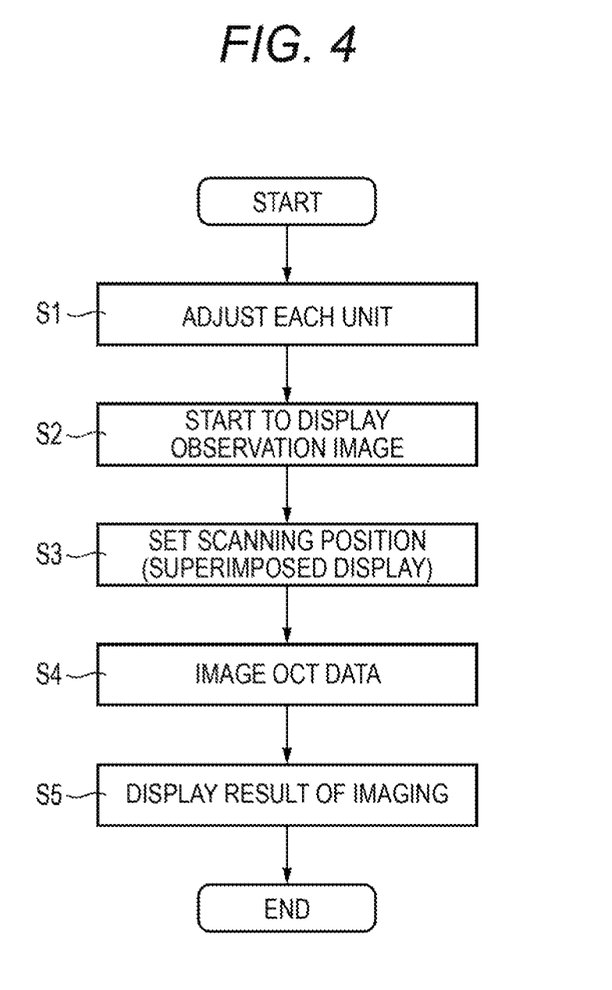
FIG. 4 is a flowchart illustrating an operation by the ophthalmologic imaging apparatus.

Next, the operation by the apparatus 1 according to the example will be described with reference to the flowchart illustrated in FIG. 4.

First, each unit of the OCT optical system 100 and the second optical system 200 is adjusted so that the fundus can be imaged (S1). In addition, as the observation image, acquisition of the front image of the fundus via the second optical system 200 is started (S2). In the adjustment of each unit (S1), for example, the alignment adjustment, the focus adjustment in the OCT optical system 100 and second optical system 200, the polarization adjustment in the OCT optical system 100, the optical path length adjustment, or the like may be appropriately performed.

<Planning of OCT Data Acquisition Position>

Next, the OCT data acquisition position may be set (S3). In the present example, the acquisition position is set as the scan line. The scan line may be set based on an operation input via the front image of the fundus displayed on the screen, for example. The front image of the fundus displayed at this time is an image acquired through the second optical system 200. In addition, the observation image may be displayed as the front image of the fundus.

The front image of the fundus is displayed after being corrected based on the association information for SLO so as to be expressed in a coordinate system that is symmetric with respect to the angle of view ($\theta x$, $\theta y$). In such front image of the fundus, the association relationship between the coordinates and the angle of view becomes a known relationship based on the association information for SLO. As an example, in the present example, a front image of the fundus in which pixels are arranged at equal intervals with respect to the angle of view is displayed.

The operation input may set at least the start point and the end point of the scan line on the front image. In this case, the control parameter (input) of the scanning unit 150 in the OCT optical system 100 is set according to the positions of the start point and the end point. As described above, since the association relationship between each coordinate and the angle of view in the front image of the fundus is known, if a scan line is set on the front image of the fundus, it is possible to obtain the value of the angle of view associated with each coordinate on the scan line. In the association information for OCT, since the association relationship between the swing angle (x, y) of the scanning unit 150 in the OCT optical system 100 and the angle of view ($\theta x$, $\theta y$) is indicated, it is possible to obtain the swing angle (x, y) of the scanning unit 150 associated with each coordinate on the scan line. By acquiring this as a control parameter of scanning unit 150, the set scan line can be scanned with the measurement light with high accuracy.

In addition, any one of a plurality of predetermined scan patterns may be selected. In this case, the scan pattern selection operation is input via the operation unit 75. Examples of the scan pattern include a raster scan (a map scan), a multi-scan in which a plurality of scan lines separated from each other are used for scanning, a cross scan in which a plurality of scan lines intersect with each other, a radial scan in which a plurality of scan lines are radially formed, and the like. In the present example, the control parameters of the scanning unit 150 may be determined for each scan pattern in advance. The swing angle of the scanning unit 150 corresponding to the start point and the end point of each scan line configuring the scan pattern, and the driving speed therebetween are determined in advance as control parameters.

Figure 5:
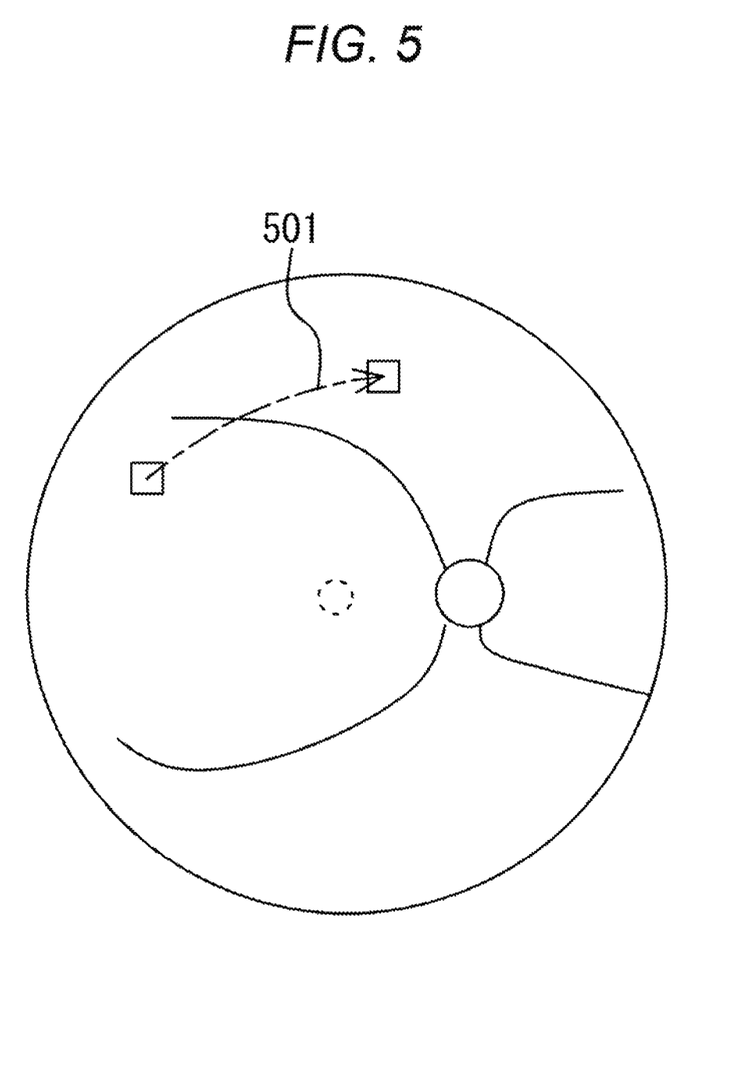
FIG. 5 is a diagram illustrating a front image of the fundus on which a graphic indicating a scan line is displayed in a superimposed manner.

When setting the scan line via the front image of the fundus, a graphic 501 indicating the scan line is displayed on the front image in a superimposed manner together with the front image of the fundus. In the present example, at this time, the graphic 501 is not necessarily indicated by a straight line, but may be indicated as a curve. That is, in the present example, each coordinate of the front image on the trajectory of the measurement light when each of the two Galvano-scanners is driven at a constant angular velocity may be obtained based on the association information for OCT and the association information for SLO, and then, a straight line or a curve passing through each coordinate may be displayed as the graphic 501. In this way, in the present example, the scan line when each of the two Galvano-scanners in the scanning unit 150 is driven at a constant angular velocity is accurately displayed by the graphic 501.

Figure 6:
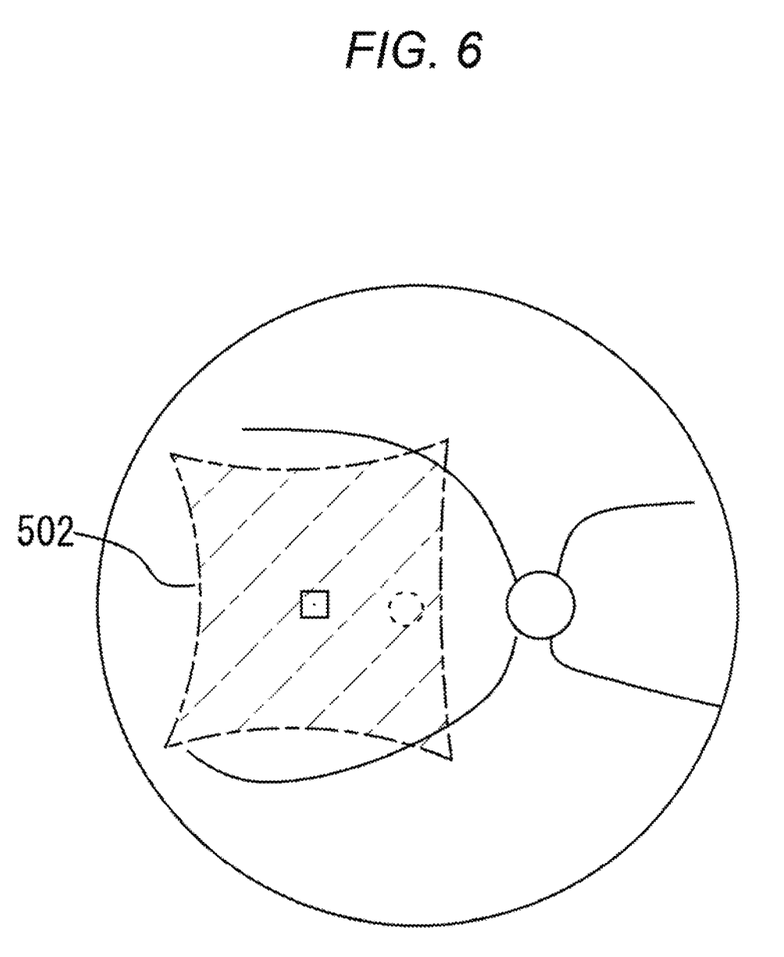
FIG. 6 is a diagram illustrating a front image of the fundus on which a second graphic indicating a region to be raster-scanned with measurement light is displayed in a superimposed manner.

Similarly, when the map scan range is set for the two-dimensional area on the front image, each coordinate of the front image corresponding to the extension of the map scan may be obtained based on the association information for OCT and association information for SLO, and then, the area surrounded by each coordinate may be displayed as a graphic 502 (refer to FIG. 6).

<Imaging OCT Data>

After setting the scan line, the fundus is scanned with the measurement light along the set scan line, and the OCT data is imaged (S4). At this time, in the present example, each of the two Galvano-scanners is driven at a constant angular velocity between the start point and the end point of the scan line. As a result, the fundus region where the scan line is superimposed on the front image is accurately traced by the measurement light.

Display Result of Imaging>

The imaged OCT data may be displayed on the monitor 80 (S5). At this time, a graphic indicating the front image of the fundus and the OCT data acquisition position (here, the scan line) may be indicated together with the OCT data. The graphic may be displayed based on the acquisition position information associated with the OCT data at the time of imaging and the association information stored in the storage unit 72 in advance. The graphic may be displayed on the front image of the fundus in a superimposed manner in the same manner as the <Planning of OCT Data Acquisition Position>. For example, as the acquisition position information, the swing angles associated with the start point and the end point of the scan line may be acquired at the time of imaging, and may be associated with the OCT data. A line passing through the position of coordinates on the front image associated with the swing angle and the position of coordinates on the front image associated with an intermediate value of the swing angle, may be obtained. A graphic indicating the above-described line may be displayed on the front image of the fundus in a superimposed manner.

Figure 7:
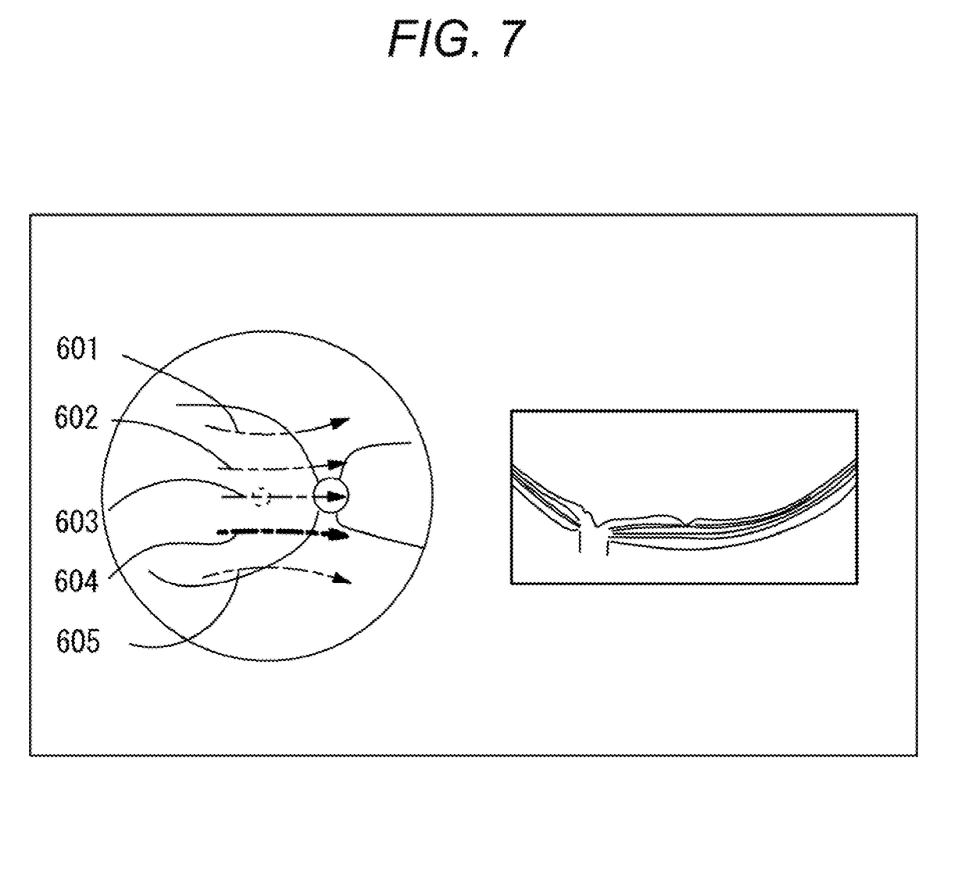
FIG. 7 is a diagram illustrating an example of a screen for confirming a result of imaging.

When the OCT data of multiple lines are imaged and some of them are displayed on the monitor 80, at least a graphic indicating the scan line of the part of the OCT data is displayed on the monitor. For example, as illustrated in FIG. 7, a plurality of graphics 601 to 605 each indicating a plurality of scan lines may be displayed in a superimposed manner, and in this case, a graphic (indicated by a reference numeral 604 in FIG. 7) corresponding to a graphic displayed as the OCT data on the monitor 80 may be displayed in a different mode from another graphic.

Modification Example

As above, the description is made based on the illustrative embodiment and the example, however, the content of the illustrative embodiment and the example can be appropriately changed in implementing the present disclosure.

For example, in the <Planning of OCT Data Acquisition Position> and the <Display Result of Imaging> in the example described above, the observation image is exemplified as the front image of the fundus on which the graphic indicating the OCT data acquisition position is displayed in a superimposed manner, but not necessarily limited thereto. Not limited to the observation image, a graphic indicating the OCT data acquisition position may be displayed on the image captured by the second optical system in a superimposed manner. In addition, a front image of the fundus of the subject eye captured by another imaging apparatus may be imported into the apparatus 1 in advance, and then, a graphic indicating the OCT data acquisition position may be displayed on the front image of the fundus in a superimposed manner. In this case, it is desirable that each area (coordinates) in the front image of the fundus captured by another imaging apparatus is associated with each area (coordinates) in the front image of the fundus by the second optical system, and the information indicating the association relationship (referred to as the third association information) is provided. Using the first to third association information, the association relationship between the coordinates on the front image of the fundus and the OCT data acquisition position by another imaging apparatus can be specified.

Figure 8:
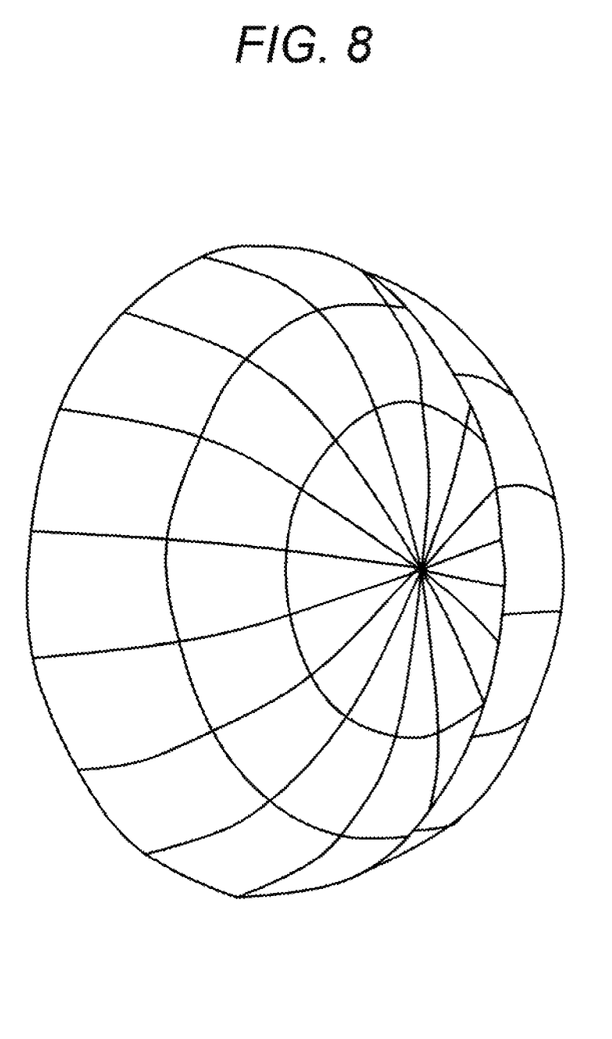
FIG. 8 is a diagram illustrating a three-dimensional model.

In addition, in the example described above, the front image is described under the assumption that the pixels are arranged at equal intervals with respect to the angle of view. If the pixels are arranged at the equal intervals with respect to the angle of view, the front image may be displayed by a three-dimensional fundus model as illustrated in FIG. 8. Each region of the three-dimensional fundus model is associated with each region and the angle of view in advance. By displaying via the three-dimensional fundus model, the examiner can more appropriately grasp the position of the scan line with respect to the fundus.

In addition, for example, in the example described above, the second optical system performs two-dimensional scanning with the light focused on the observation surface in a spot shape. However, the second optical system is not limited thereto, and may be a so-called slit scan (line scan) optical system or a non-scanning type optical system.

What is claimed is:

1. An ophthalmologic imaging apparatus comprising:
    an OCT optical system for acquiring OCT data of a tissue of a subject eye based on a spectral interference signal of measurement light emitted to the tissue and reference light;

a second optical system for acquiring a front image of the tissue;

an optical element having asymmetry and being arranged on a common optical path of the OCT optical system and the second optical system; and a controller comprising a processor and memory with programming that matches an OCT data acquisition position with coordinates of the front image, accounting for at least a difference in distortion caused by the optical element between the OCT optical system and the second optical system; and wherein the optical element is arranged on a common optical path of the OCT optical system and the second optical system; and the optical element comprises a dichroic mirror that combines an optical path of the OCT optical system and an optical path of the second optical system.

2. The ophthalmologic imaging apparatus according to claim 1, wherein the OCT optical system comprises an optical scanner for scanning the tissue with the measurement light, wherein the memory of the controller comprises programming to match the OCT data acquisition position with the coordinates of the front image based on association information, and wherein the association information is set in advance for each swing angle in the optical scanner and represents a non-linear positional relationship between a swing angle and the coordinates of the front image.

3. The ophthalmologic imaging apparatus according to claim 2, wherein the association information includes:
  a first association information representing the positional relationship between the swing angle in the optical scanner and an angle of view; and
  a second association information representing a positional relationship between the coordinates on the front image and the angle of view, and
  wherein the swing angle in the optical scanner can be matched with the coordinates of the front image via the angle of view.

4. The ophthalmologic imaging apparatus according to claim 1, wherein the memory of the controller comprises programming to display a graphic indicating the OCT data acquisition position on the front image in a superimposed manner by matching the OCT data acquisition position with the coordinates of the front image.

5. The ophthalmologic imaging apparatus according to claim 4, wherein the memory of the controller comprises programming to display a scan line as the graphic shown as curve on the front image in a superimposed manner, the scan line being set at a position away from an optical axis and being along a main scanning line.

6. The ophthalmologic imaging apparatus according to claim 4, wherein the OCT optical system comprises an optical scanner for scanning the tissue with the measurement light, and wherein the memory of the controller comprises programming to generate a trajectory of the measurement light as the graphic indicating a scan line connecting two points based on matched OCT data acquisition position with coordinates of the front image, the trajectory being drawn when the optical scanner is driven at a constant angular velocity in scanning between the two points.

7. The ophthalmologic imaging apparatus according to claim 4, wherein the memory of the controller comprises programming to generate the front image in which pixels are arranged at equal intervals with respect to an angle of view to display the graphic indicating the acquisition position on the front image in a superimposed manner.

8. The ophthalmologic imaging apparatus according to claim 1, comprising an objective optical system arranged eccentrically with respect to optical axes of the OCT optical system and the second optical system.

* * * * *